United States Patent [19]

Frick

[11] 4,397,704
[45] Aug. 9, 1983

[54] METHOD AND APPARATUS FOR APPLYING DISCRETE LENGTHS OF ELASTIC STRIP MATERIAL TO A CONTINUOUSLY MOVING WEB

[75] Inventor: Richard H. Frick, Neenah, Wis.

[73] Assignee: Kimberly-Clark Corporation, Neenah, Wis.

[21] Appl. No.: 198,778

[22] Filed: Oct. 20, 1980

[51] Int. Cl.³ .............................................. B32B 31/04
[52] U.S. Cl. .................................... 156/201; 156/210; 156/256; 156/265; 156/285; 156/462; 156/471; 156/472; 156/473; 156/517; 156/519; 156/552
[58] Field of Search ............... 156/205, 208, 210, 256, 156/265, 285, 470, 471, 472, 473, 459, 462, 517, 519, 552, 553, 163, 164, 269, 297, 302, 518, 520, 553, 464, 474, 201; 428/181, 182, 186

[56] References Cited

U.S. PATENT DOCUMENTS

| | | | |
|---|---|---|---|
| 3,026,231 | 3/1962 | Chavannes | 156/210 |
| 3,854,861 | 12/1974 | Worrall | 156/210 |
| 3,957,570 | 5/1976 | Helm | 156/552 |
| 4,025,373 | 5/1977 | Hirsch et al. | 156/256 |
| 4,177,102 | 12/1979 | Tokuno | 156/285 |
| 4,240,866 | 12/1980 | Rega | 156/519 |
| 4,285,747 | 8/1981 | Rega | 156/552 |
| 4,297,157 | 10/1981 | Uliet | 156/265 |

Primary Examiner—Caleb Weston
Attorney, Agent, or Firm—Richard C. Ruppin

[57] ABSTRACT

A method and apparatus for applying discrete lengths of elastic strip material to predetermined areas of a continuously moving web by corrugating the web and applying the discrete lengths of substantially unstretched adhesively coated elastic over the corrugations in predetermined areas, bonding the elastic to the areas, and withdrawing the web from the corrugations to stretch the elastic; and the conformable garment produced thereby which may be in the form of an elasticized leg disposable diaper.

14 Claims, 10 Drawing Figures

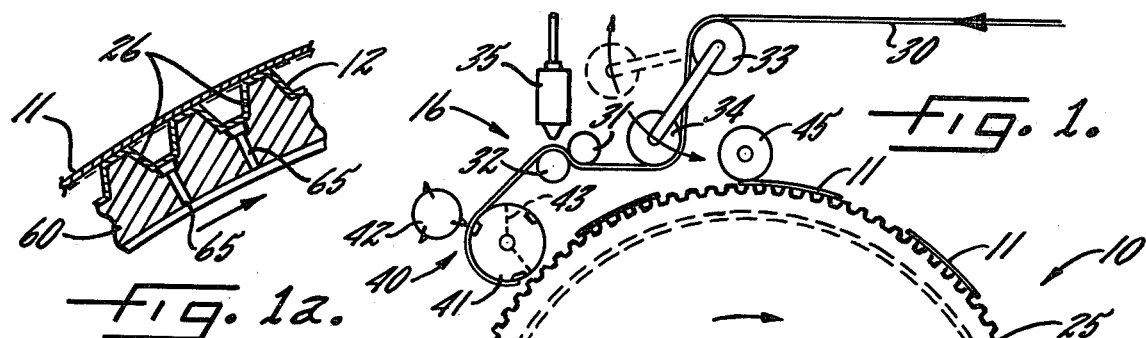
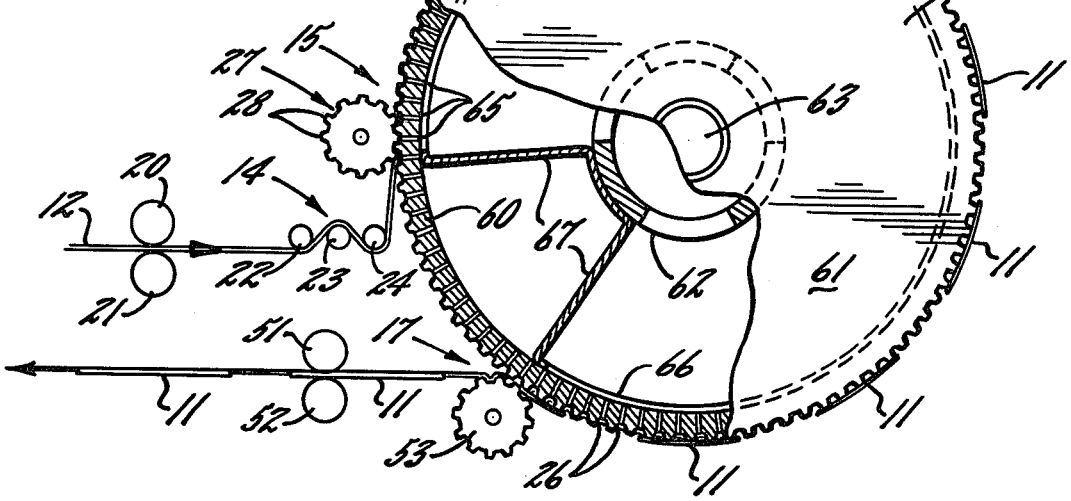
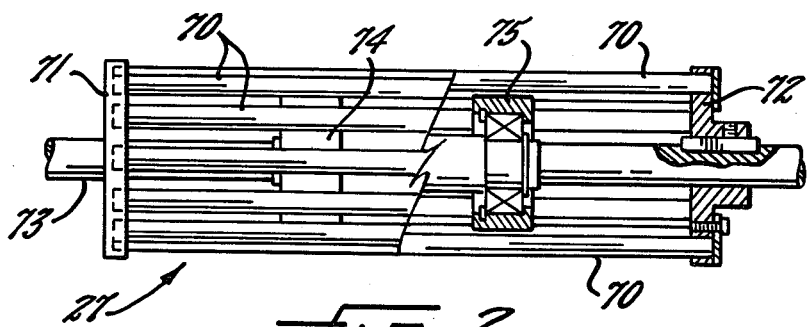
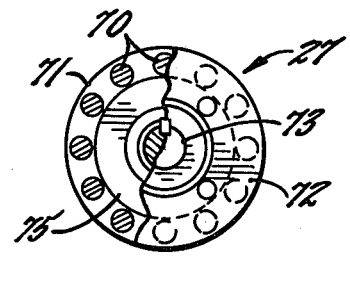
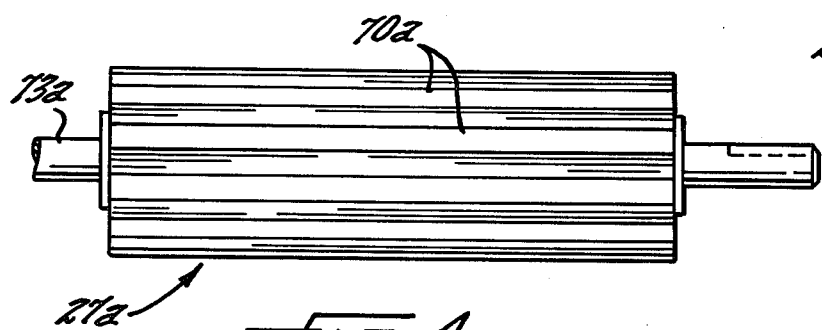
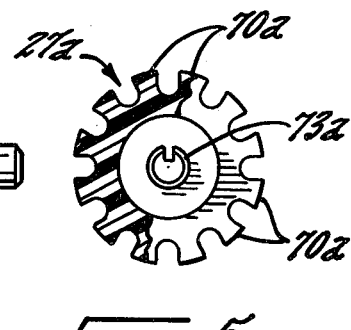

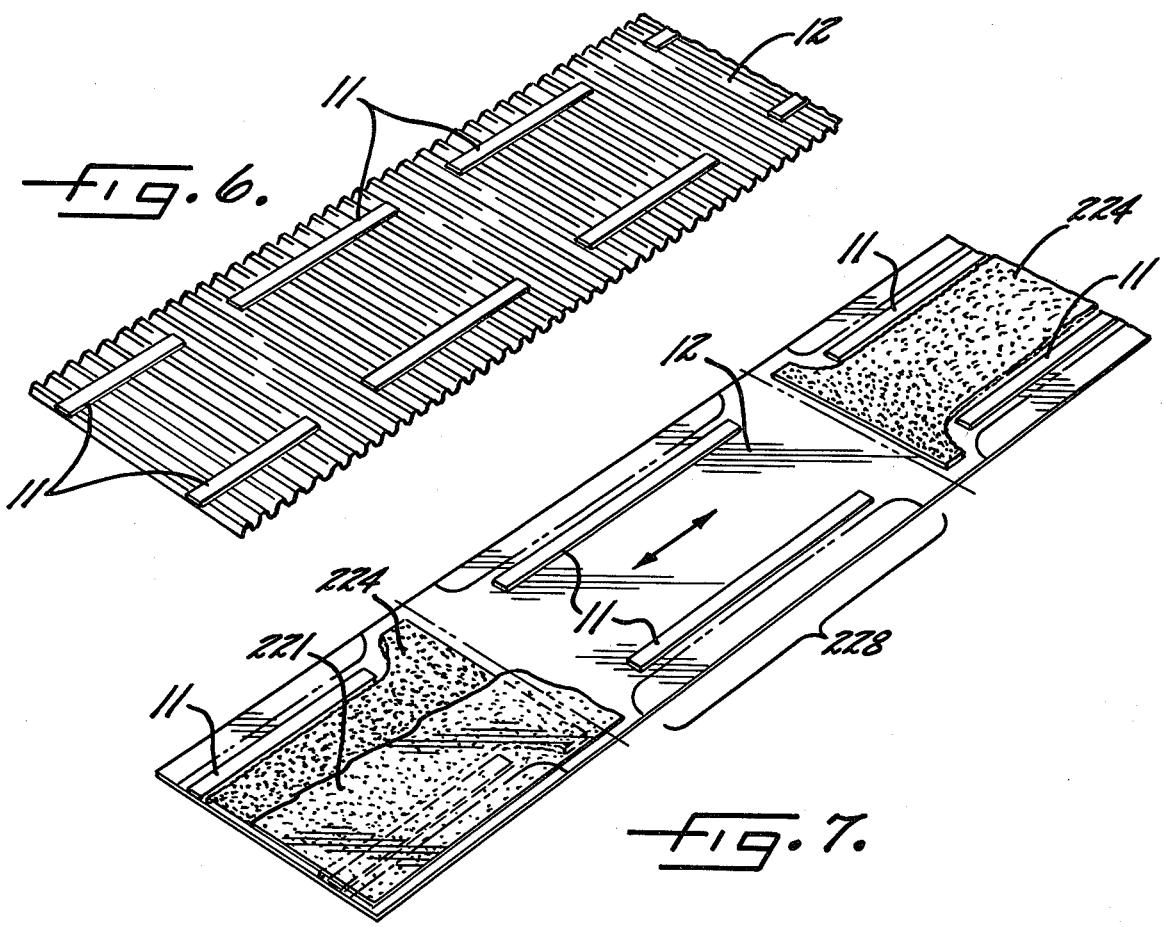
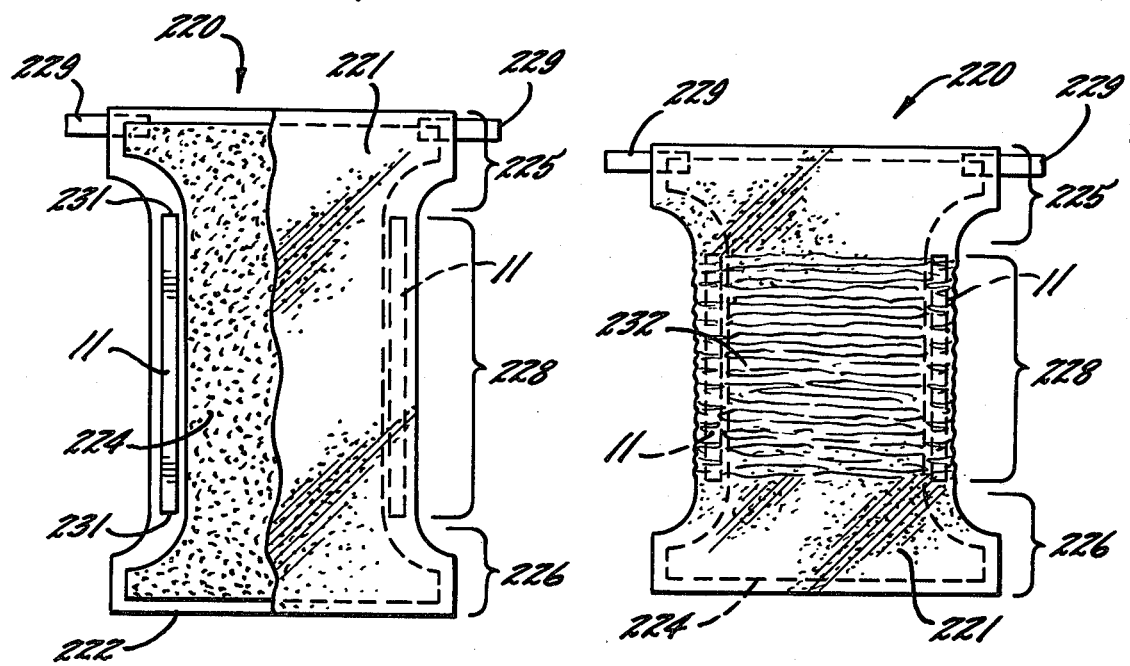

METHOD AND APPARATUS FOR APPLYING DISCRETE LENGTHS OF ELASTIC STRIP MATERIAL TO A CONTINUOUSLY MOVING WEB

FIELD OF THE INVENTION

The present invention relates in general to methods and apparatus for applying discrete lengths of elastic material to predetermined areas of a continuously moving web, on a high speed production basis, and to conformable garments produced thereby; such, for example, as disposable diapers having discrete elasticized portions in the leg openings thereof.

BACKGROUND OF THE INVENTION

Conventionally, conformable garments having discrete elasticized areas have been formed in a wide variety of ways and utilizing a wide variety of materials. In the past decade, or so, disposable diapers have become increasingly popular. More recently, such disposable diapers have been provided with elasticized leg openings to enhance both their appearance and fit.

One such elastic legged diaper is disclosed in Buell U.S. Pat. No. 3,860,003; while Buell U.S. Pat. No. 4,081,301 describes a process and apparatus for making such diapers. Another method of making elasticized products is disclosed in Bourgeois U.S. Pat. No. 3,828,367. Other elastic legged disposable diapers are disclosed in Woon et al. U.S. Pat. No. 4,050,462 and in copending Sigl U.S. application Ser. No. 094,421, filed Nov. 15, 1979; Ryan et al. U.S. application Ser. No. 135,255, filed Apr. 4, 1980; and Frick U.S. application Ser. No. 181,821, filed Aug. 27, 1980, all of which applications are assigned to the assignee of the present application. Still other examples of elasticized diapers are disclosed in British application Nos. GB 2010628A and GB 2011778A; Australian application No. 43750/79; and South African application No. 77/4456.

While the foregoing elastic legged diapers and the methods and apparatus for making them have met with some success, there remains the desire to: improve the fabrication techniques for making elastic legged diapers and other conformable garments; reduce the amount of elastic required; and, improve the product made thereby in terms of both cost and functionality.

SUMMARY OF THE INVENTION

It is the general aim of the present invention to provide an improved method and apparatus for making conformable garments having elasticized areas on a high speed production basis which not only decreases the amount of elastic material required but which also provides improved product characteristics, particularly in terms of bonding discrete lengths of the elastic material in an unstretched condition to corrugated web material to provide uniform gathering and to prevent creep and separation thereof from the garment material. More particularly, and, in the context of a disposable diaper with elasticized portions in the leg opening areas, the method and apparatus of the present invention provides for applying discrete lengths of unstretched elastic strip material to predetermined longitudinal areas of a continuously moving web of material such as the impervious backing layer of a disposable diaper to form elasticized leg openings between non-elasticized, waist band portions by corrugating the backing layer prior to the application of unstretched, adhesively coated discrete lengths of elastic to the corrugated web material and bonding the elastic in those predetermined areas followed by removing the web from the corrugations and extending the web to stretch the elastic strips.

The method and apparatus of the invention are further characterized by their ability to utilize natural, synthetic or extruded elastic material and to operate at high speed production rates and the resulting product has improved characteristics in terms of both cost and functional effectiveness over the prior art.

These and other objects and advantages of the present invention will become more readily apparent upon reading the following detailed description and upon reference to the attached drawings, in which:

DESCRIPTION OF THE DRAWINGS

FIG. 1 is a simplified and somewhat schematic side elevational view, with certain portions broken away, of the web corrugating drum and elastic application mechanism of the present invention;

FIG. 1a is an enlarged fragmentary section of the corrugating drum showing the web drawn into the grooves and a portion of the elastic strip material applied to the tops of the corrugations;

FIG. 2 is an enlarged side elevational view, partially in section, of one embodiment of the roll for pressing the web into the grooves of the corrugating drum shown in FIG. 1;

FIG. 3 is an end view of the roll shown in FIG. 2;

FIG. 4 is an enlarged side elevational view of another embodiment of the pressing roll;

FIG. 5 is an end view, partially in section, of the roll shown in FIG. 4;

FIG. 6 is a perspective view illustrating a web of material having discrete lengths of elastic material bonded thereto in predetermined longitudinal areas, with the web here illustrated in corrugated condition and the elastic strips in a substantially unstretched condition, which conditions would normally occur while the web and strips were on the corrugating drum.

FIG. 7 is a perspective view of a continuous web of garment material such as for making a series of disposable diapers which are cut from the web along the dash lines, with the backing web extended longitudinally to stretch the elastic strips, and also illustrating further diaper components such as the fluff batt filler and pervious cover sheet;

FIG. 8 is a plan view illustrating a conformable garment having discrete elasticized areas and embodying features of the present invention, with the exemplary garment here illustrated comprising a disposable diaper having portions cut away to illustrate construction details, but with the elastically extendible member shown in the fully extended condition which it would normally occupy only during the manufacturing process; and FIG. 9 is a plan view of the exemplary diaper shown in FIG. 8, here illustrating the diaper product following the final separation step in the manufacturing process wherein individualized diapers are cut from a continuous web and with the diaper here being illustrated with the elastically extendible member in its normal relaxed or unextended condition.

While the invention is susceptible of various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents and alternatives falling within the spirit and scope of the invention as defined in the appended claims.

DETAILED DESCRIPTION

Referring now to the drawings, there is schematically shown in FIG. 1, an exemplary apparatus 10 embodying features of the present invention for applying discrete lengths of elastic 11 to a continuous web 12 of garment material or the like. In its general arrangement, the apparatus 10 includes a web supply section 14, a corrugating section 15, an elastic supply and application section 16 and a web takeoff section 17. At the web supply section 14, a pair of drive rolls 20, 21 feed the web 12 at a predetermined rate to web tensioning rolls 22, 23 and 24 and then into the corrugating section 15.

In accordance with the present invention, the corrugating section 15 includes a substantially cylindrical drum 25 having a multiplicity of substantially uniform parallel, longitudinally extending grooves 26 formed in the surface of the drum and a cooperating pressing roll 27 having longitudinally extending teeth 28 for pressing the web 12 into the grooves 26 so as to corrugate the web. A continuous strip of elastic 30 is drawn into the elastic supply and application section 16 by a pair of pull rolls 31 and 32 with the elastic 30 in substantially unstretched condition and under just enough tension, such as by dancer rolls 33 and 34, as to maintain control over the elastic strip at relatively high production speeds.

After the elastic strip 30 exits from the nip of the pull rolls 31, 32 it passes under an adhesive applicator 35, shown here in the form of a nozzle, where adhesive is applied to the elastic strip 30. It will be understood that the adhesive may be applied in a continuous bead or in an interrupted but substantially regular pattern of dots. Alternatively, the adhesive could be applied by a roll type applicator in either a continuous or intermittent fashion such as by a print roll. In any event it is preferred to apply the adhesive substantially continuously along the length of the elastic strip 30.

To apply discrete lengths 11 of elastic to the web 12 on the corrugating drum 25, the adhesively coated strip of elastic 30 is fed into a cutting mechanism 40, shown here in its preferred embodiment as an anvil roll 41 and a knife roll 42 which rotate in timed relation to the rotation of the corrugating drum 25. Preferably, the anvil roll 41 and knife roll 42 are formed to make a plurality of cuts per revolution, desirably three as in the illustrated embodiment, and the cutting rolls 41 and 42 rotate at a peripheral speed about half that of the corrugating drum 25. This provides that the discrete lengths of elastic 11 are applied to the corrugated web 12 in predetermined spaced apart areas.

For facilitating transfer of the severed length of elastic 11 to the web 12, a vacuum is preferably drawn within the anvil roll 41. A stationary internal vane 43 may be employed to control the relative portions of the surface of the anvil roll 41 on which the vacuum is effective. Preferably, the vacuum is also effective on the upper surface of the anvil roll 41 and this serves to control the end of the elastic strip 30. The cutting rolls 41, 42 rotate at the same surface speed as the pull rolls 31, 32 and at half the surface speed of the corrugating drum 25 in order to provide the predetermined spacing of the elastic length 11 as mentioned above. Additionally, the space between the engaged knife and anvil of the cutting rolls 41, 42 and corrugating drum 25 is such that the adhesive on the strip 11 contacts the web 12 to remove elastic strip 11 from anvil roll 41 after it is cut by the knife roll 42. In other words, the circumferential length of arc on anvil roll 41 is such that the cut occurs just before the elastic strip 11 contacts the web 12.

In order to bond the elastic lengths 11 to the corrugated web 12, a calender roll 45 is preferably provided to apply pressure against the elastic 11, the web 12 and the drum 25. It will be understood, of course, that additional calender rolls can be employed, if desired, or eliminated depending upon the type of adhesive used and the operating parameters, particularly speed and temperature that are involved. In any event it is desired to have the elastic strips 11 securely bonded to the corrugated web 12 before the web is drawn off the corrugating drum 25.

The web 12 with attached lengths of elastic 11 is removed from the corrugating drum 25 at the web takeoff section 17. For this purpose, a pair of pull rolls 51 and 52 and a stripping roll 53 are provided. The pull rolls 51, 52 are driven at the same speed as the web feed rolls 20 and 21 and thus the exit speed of the web is the same as its entry speed. This pulls the corrugations out of the web 12 and stretches the elastic lengths 11 as shown at the lower left in FIG. 1. The stripper roll 53 controls the point at which the web 12 leaves the drum 25 and prevents the web from being pulled out of the grooves 26 prematurely. The pull rolls 51, 52 also serve to nip the elastic lengths 11 to the web 12 and thus further insure adequate bonding therebetween.

The corrugating drum 25 is preferably formed of a substantially hollow shell 60 with fixed end plates 61 (only one of which is shown) mounted by suitable hubs 62 and bearings for rotation on a shaft 63. The drum is rotated by suitable drive means (not shown). The grooves 26 in the shell 60 of the drum 25 are preferably formed with substantially equal hill and valley portions such that about half of the material is pressed into the grooves. Thus, the uncorrugated web material has a mean length of about a 2:1 ratio compared to the mean length of the corrugated material. This means that the peripheral speed of the corrugating drum is only about one-half the speed of the web as it is fed into the corrugating section.

To help pull the web 12 into the grooves 26, a vacuum is preferably drawn within the drum 25 and is communicated to the bottoms of the grooves 26 through a plurality of apertures 65 (See FIG. 1a). Within the drum 25 means are provided for isolating the vacuum to an area extending (in the direction of rotation) from substantially adjacent the web pressing roll 27 to substantially adjacent the stripping roll 53. As shown in FIG. 1, the shell 60 of the drum 25 rotates around an internal sleeve 66 fixed to the shaft 63. The sleeve is provided with radially extending webs 67 which serve as internal vanes to isolate the effective vacuum within the drum.

Turning now to FIGS. 2 and 3, one embodiment of the web pressing roll 27 is shown. The roll 27 basically includes a plurality of elongated rods 70 mounted in end hubs 71, 72 keyed to a central shaft 73. The rods 70 act as teeth which mate with the grooves 26 in the corrugating drum 25 and press the web material 12 into the grooves to corrugate the material. In the preferred embodiment, the roll 27 includes a pair of internal hubs 74, 75 mounted on the shaft 73 which serve to prevent excessive deflection of the rods 70.

Another embodiment of pressing roll 27a is shown in FIGS. 4 and 5. Here the roll 27a is formed of plastic with elongated teeth 70a in the outer surface thereof. The roll 27a includes a central shaft 73a.

Referring to FIG. 6, the corrugated web 12 is shown with a plurality of discrete lengths of substantially unstretched elastic 11 bonded thereto at predetermined longitudinal locations. It will be appreciated, of course, that this generally planar perspective view of the corrugated web 12 is simply illustrative of what the web on the corrugating drum 25 would look like, if laid out flat. In actual practice, the corrugations in the web 12 are pulled out substantially flat, when the web is removed from the drum 25 by the pull rolls 51 and 52 as shown in FIG. 1.

The web 12 in its extended condition with the corrugations pulled out and the elastic bands 11 stretched is shown in the central portion of FIG. 7. Preferably, the elastic bands 11 in their stretched condition are about twice as long as the unstretched discrete lengths 11 in FIG. 2. The web 12 with attached discrete lengths of elastic 11 is particularly suited for making conformable garments such as elasticized legged diapers at high production speeds with the addition of a fluff batt 224 and a permeable cover sheet 221, to be described in more detail below.

Referring now to FIGS. 8 and 9, the present invention has been illustrated in connection with the formation of such a conformable garment which is shown and described here as a disposable diaper, generally indicated at 220. Although the exemplary diaper 220 is here illustrated in the form of a finished product severed from the continuous web of products made in a high speed continuous production operation, it has, for purposes of facilitating a complete understanding of the invention, nevertheless been shown in the stretched or fully extended position that the product would normally occupy only just prior to being severed from the continuous web upon completion of the manufacturing process.

In keeping with the present invention, the illustrative diaper 220 is of elongate generally "I" shape, and includes a fluid permeable facing 221, a fluid impervious backing sheet 222, and a highly absorbent batt 224 sandwiched between the facing and backing sheets 221, 222 respectively.

The specific components used to form the exemplary diaper may be any of the types commonly used for such purposes. For example, the fluid pervious facing sheet may be any soft, flexible porous sheet which permits the passage of fluids therethrough including hydrophobic or hydrophilic non-woven webs, wet strength papers, spunwoven filament sheets, and the like. A particularly suitable sheet is one made of spunwoven polypropylene filaments with spot embossing, and preferably with a perforated surface or suitable surfactant treatment to aid fluid transfer. The fluid impermeable backing sheet 222 is preferably a thin plastic film such as polyethylene, polypropylene, polyvinylchloride, or the like and would generally be on the order of one mil in thickness. The sheet is preferably opaque with an embossed or matte surface.

The exemplary diaper shown in FIGS. 8 and 9 is divided into waistband sections 225 and 226 at each end and a central narrowed-down crotch section 228 disposed between the waistband sections. During use, waistband section 225 would normally be disposed at the back of the infant and may be referred to herein as the back portion of the diaper, while section 226 would normally be disposed at the front and may be referred to herein as the front portion of the diaper. Conventional pressure sensitive tapes 229 are attached to the backing sheet 222 near the edges of waistband section 225 for fastening purposes, although other suitable fastening means may be employed. Such tapes are usually attached near the back portion of the diaper.

One surface of absorbent batt 224 is bonded to backing sheet 222 and/or to facing sheet 221 in at least the crotch section 228. Such bonding may be done by the use of strips of double-faced pressure sensitive adhesive, by overall or patterned heat sealing, by extruded adhesive beads, by a printed pattern of adhesive, or the like. One desirable type of adhesive is an atactic polypropylene based hot melt adhesive of the type known as A337S manufactured by Eastman Chemical Co. of Kingsport, Tenn. Generally, attachment should be such that when the sheet to which the batt 224 is bonded is constricted in its longitudinal direction by elastic means 11 disposed near the batt edges, the batt will also be constricted and convoluted thereby.

As previously indicated, the elastic means 11 is fully stretched and under tension only during the manufacturing process. The diaper as shown for convenience in its fully extended condition in FIG. 8, is in a condition which would normally occur only during the manufacturing process when a series of diapers are attached to each other in the form of a continuous strip. When this continuous strip is cut into individual diapers, the elastic 11 is thus relieved of its tension and contracts from its fully extended condition, causing the crotch section 228 of the diaper to contract in the elasticized area as shown in FIG. 9. As indicated therein, waistband sections 225 and 226 are not constricted and remain substantially flat or planar because the end portions 231 of the elastic means 11 do not extend into these sections even during fabrication. When the relatively narrow crotch section 228 is constricted by the contracted elastic means 11 at each edge, the crotch section develops a multiplicity of gross transverse rugosities 232. Stated another way, crotch section 228 is reduced in length but still contains the same amount of absorbent material. Accordingly, the absorbent batt 224 in the crotch area 228 is made effectively thicker because of the adjoining hills and valleys of which the transverse rugosities 232 are comprised and, therefore, will have more absorbent capacity per unit area than a batt of the same original thickness has in its initial planar form.

In addition to making the diaper 220 effectively more absorbent in the crotch area 228, the cushioning effect of the pad element forming the rugosities 232 serves to relieve some of the pressure of the tensioned elastic means 11 where it presses the diaper into contact with the infant's skin when the diaper is worn. Accordingly, even though the elastic means 11 will be under tension in the crotch area 228 due to its being partially stretched out when the diaper is applied to the child, the transverse rugosities 232 remaining in the absorbent pad act as cushions and tend to reduce the possibility of the elastic indenting or marking the skin. Such indentation or marking is more likely to happen when the tensioned elastic means 11 is part of a thin flexible flap as commonly employed in the prior art, such as in the aforesaid Buell U.S. Pat. No. 3,860,003, thus permitting more intimate contact with the skin.

An improved and particularly preferred embodiment of an elasticized leg diaper which, when worn, forms an absorbent pocket with planar sides in the crotch area is disclosed in the aforementioned copending Ryan et al. U.S. application Ser. No. 138,255, filed Apr. 7, 1980, and assigned to the assignee of the present application and which is hereby incorporated by reference. As disclosed in the above-mentioned Ryan et al. application, the pocket has flex regions in the crotch area of the diaper which define a bottom crotch profile and elastic edges which encircle the leg of the baby and semirigid absorbent-containing planar sides extending upward from the flex regions to the elastic edges. The diaper at its lowest profile in the crotch area is generally upwardly arcuate when the baby is standing and the stiffness of the sides is generally correlative of a Taber stiffness value of at least seven gm-cms for the absorbent material located therein.

Improved garments having discrete elasticized areas such, for example, as the disposable diaper 220 described above in connection with FIGS. 8 and 9 may be formed with elastic strips 11 of natural rubber; thermoplastic elastomeric ribbons having a polyurethane base such as TUFTANE ® manufactured by B. F. Goodrich Co.; or, from extruded elastic such as FULLASTIC No. 907-67-2 hot metal adhesive from the Fuller Elastic Company, as taught in my copending application Ser. No. 181,821, which is incorporated herein by reference.

From the foregoing it will be seen that the present application discloses an improved method and apparatus for applying discrete lengths of unstretched elastic material only to predetermined areas of garment material at high production speeds with consequent savings of elastic, adhesive or both and with the elastic securely anchored along its entire length to provide an improved elasticized garment.

I claim as my invention:

1. Apparatus for applying discrete lengths of elastic strip material to predetermined longitudinal areas of a continuously moving web comprising, in combination:
    a substantially cylindrical drum having a multiplicity of substantially uniform parallel grooves, extending longitudinally and formed in the surface of said drum, and means for rotating said drum,
    means for feeding said web to said rotating drum at a predetermined rate and for pressing said web into said grooves so as to corrugate said web,
    means for supplying a continuous strip of adhesively coated elastic material for application to said web on said drum,
    means for severing said adhesively coated elastic material into discrete lengths before transferring said discrete lengths to predetermined areas of web on said drum in timed relation to the rotation of said drum,
    means for bonding said discrete lengths of elastic to said web on said drum with said adhesive interposed between said elastic lengths and said web, and
    means for removing said web and attached discrete lengths of elastic from said drum and pulling out said corrugations pressed into said web so as to stretch said discrete length of elastic bonded to said web and to return said web in areas between successive ones of said discrete lengths of elastic to a substantially flat uncorrugated condition.

2. Apparatus as defined in claim 1 wherein said means for pressing said web into said grooves includes a roll having a plurality of longitudinally extending teeth which engage said grooves.

3. Apparatus as defined in claim 2 wherein said teeth are formed of long rods carried by spaced apart end hubs.

4. Apparatus as defined in claim 2 wherein said roll is formed of a plastic material with said teeth formed on the outer surface thereof.

5. Apparatus as defined in claim 1 including means for drawing a vacuum in the interior of said drum and for communicating said vacuum to the bottom of said grooves to help draw said web into said grooves.

6. Apparatus as defined in claim 5 including means for isolating said vacuum within said drum to an area extending from substantially adjacent said web pressing means to substantially adjacent said web removing means.

7. Apparatus as defined in claim 1 wherein said severing means includes an anvil roll and a knife roll rotatable in timed relation to one another.

8. Apparatus as defined in claim 7 wherein said anvil roll and knife roll are formed to make a plurality of cuts per revolution.

9. Apparatus as defined in claim 7 including means for drawing a vacuum in a predetermined arc within said anvil roll to transfer said discrete lengths of elastic to said corrugated web and to control the free end of said continuous strip of elastic.

10. Apparatus as defined in claim 1 wherein said elastic supply means includes an adhesive applicator immediately upstream of said severing means.

11. A method of applying discrete lengths of elastic strip material to predetermined areas of a continuously moving web comprising the steps of:
    feeding the web material at a predetermined rate to a rotating corrugating drum having a multiplicity of substantially uniform parallel grooves in the surface thereof,
    pressing the web into said grooves,
    drawing a continuous strip of adhesively coated elastic material from a supply source,
    severing a continuous strip of adhesively coated elastic into discrete lengths,
    transferring said discrete lengths of elastic to said web on said drum at predetermined intervals,
    bonding said discrete lengths of elastic to said web on said drum, and
    removing said web and attached discrete lengths of elastic from said drum and pulling out said corrugations pressed into said web so as to stretch said discrete lengths of elastic bonded to said web and to return said web in areas between successive ones of said discrete lengths of elastic to a substantially flat uncorrugated condition.

12. The method defined in claim 11 including drawing a vacuum in the bottom of said corrugating drum grooves to help pull said web into said grooves.

13. The method defined in claim 11 wherein said severing of said elastic strip includes passing said strip between an anvil roll and a knife roll rotatable in timed relation to one another and formed to make a plurality of cuts per revolution at a peripheral speed less than the peripheral speed of said corrugating drum.

14. The method defined in claim 13 including drawing a vacuum in a predetermined arc within said anvil roll for transferring said discrete lengths of elastic to said web on said drum and to control the free end of said continuous strip of elastic.

* * * * *